US010066188B2

(12) United States Patent
Vautravers et al.

(10) Patent No.: US 10,066,188 B2
(45) Date of Patent: Sep. 4, 2018

(54) AROMA CHEMICALS

(71) Applicant: BASF SE, Ludwigshafen (DE)

(72) Inventors: Nicolas Vautravers, Mannheim (DE);
Joaquim H. Teles, Waldsee (DE);
Nicolas Marion, Mannheim (DE)

(73) Assignee: BASF SE (DE)

( * ) Notice: Subject to any disclaimer, the term of this patent is extended or adjusted under 35 U.S.C. 154(b) by 0 days.

(21) Appl. No.: 15/106,048

(22) PCT Filed: Dec. 19, 2014

(86) PCT No.: PCT/EP2014/078689
§ 371 (c)(1),
(2) Date: Jun. 17, 2016

(87) PCT Pub. No.: WO2015/091924
PCT Pub. Date: Jun. 25, 2015

(65) Prior Publication Data
US 2016/0312149 A1  Oct. 27, 2016

(30) Foreign Application Priority Data
Dec. 20, 2013 (EP) .................... 13199171

(51) Int. Cl.
C11B 9/00 (2006.01)
C07C 67/303 (2006.01)
C07C 67/03 (2006.01)
C07C 67/475 (2006.01)
A23L 27/20 (2016.01)

(52) U.S. Cl.
CPC ........ *C11B 9/0019* (2013.01); *A23L 27/2028* (2016.08); *C07C 67/03* (2013.01); *C07C 67/303* (2013.01); *C07C 67/475* (2013.01); A23V 2002/00 (2013.01)

(58) Field of Classification Search
CPC ..... C11B 9/0019; C07C 67/475; C07C 67/03; C07C 67/303
See application file for complete search history.

(56) References Cited

U.S. PATENT DOCUMENTS

| 2,244,487 | A | 6/1941 | Crawford |
| 4,451,665 | A | 5/1984 | Nugent |
| 4,528,124 | A | 7/1985 | Sturm et al. |
| 4,594,447 | A | 6/1986 | Wilke et al. |
| 4,668,433 | A | 5/1987 | Ochsner |
| 5,453,535 | A | 9/1995 | Fischer |
| 5,508,422 | A | 4/1996 | Teles et al. |

FOREIGN PATENT DOCUMENTS

| DE | 3336691 A1 | 4/1985 |
| EP | 0103125 A2 | 3/1984 |
| EP | 0177807 | * 4/1986 |
| EP | 0177807 A2 | 4/1986 |
| EP | 0587044 A2 | 3/1994 |
| EP | 0632010 A1 | 1/1995 |
| FR | 2 524 341 A1 | 10/1983 |
| JP | S-5492636 A | 7/1979 |
| JP | H1135969 A | 2/1999 |
| JP | H1171312 A | 3/1999 |
| WO | WO-9716523 A1 | 5/1997 |

OTHER PUBLICATIONS

International Preliminary Report on Patentability dated Jun. 21, 2016 from corresponding International Application No. PCT/EP2014/078689.
International Search Report for PCT/EP2014/078689 dated Apr. 8, 2015.
Written Opinion of the International Searching Authority for PCT/EP2014/078689 dated Jun. 25, 2015.
Albisetti, C., et al., "Dimers of Methacrylic Compounds", Journal of the American Chemical Society, vol. 78, No. 2, (1956), pp. 472-475.
Biju, A., et al., "N-Heterocyclic Carbene Catalyzed Umpolung of Michael Acceptors for Intermolecular Reactions", Angewandte Chemie International Edition, vol. 50, No. 36, (2011), pp. 8412-8415.
Dunoguès, J., et al., "C-Silylation d'Esters par le Systeme Me$_3$SiCl/Li/THF", Journal of Organometallic Chemistry, vol. 66, No. 2, (1974), pp. C39-C42.
Kato, T., et al., "Experimental Mechanistic Studies of the Tail-to-Tail Dimerization of Methyl Methacrylate Catalyzed by N-Heterocyclic Carbene", The Journal of Organic Chemistry, vol. 78, No. 17, (2013), pp. 8739-8747.
Matsuoka, S., et al., "Organocatalytic Tail-to-Tail Dimerization of Olefin: Umpolung of Methyl Methacrylate Mediated by N-Heterocyclic Carbene", Organic Letters, vol. 13, No. 14, (2011), pp. 3722-3725.
Naruchi, K., et al., "Thermal Dimerization of Calcium Methacrylate", Nippon Kagaku Kaishi, vol. 1976, No. 11, (1976), pp. 1794-1796.
Qi, G., et al., "Isospecific polymerizations of alkyl methacrylates with a bis(alkyl)Yb complex and formation of stereocomplexes with syndiotactic poly(alkyl methacrylate)s", Tetrahedron, vol. 59, No. 52, (2003), pp. 10409-10418.

* cited by examiner

Primary Examiner — Shirley V Gembeh
(74) Attorney, Agent, or Firm — Drinker Biddle & Reath LLP

(57) ABSTRACT

The present invention relates to the use of diesters of 2,5-dimethyl-2-hexenedioic acid, 2,5-dimethyl-3-hexenedioic acid and 2,5-dimethyladipic acid or a mixture thereof as a fragrance or as flavor, to a method for imparting or modifying a scent or a flavor to a composition by including said compounds into such composition, to a fragrance containing composition and/or a fragrance material containing said compounds and to a process for preparing diesters of 2,5-dimethyladipic acid.

20 Claims, No Drawings

AROMA CHEMICALS

CROSS-REFERENCE TO RELATED APPLICATIONS

This application is a national stage application (under 35 U.S.C. § 371) of PCT/EP2014/078689, filed Dec. 19, 2014, which claims benefit of European Application No. 13199171.3, filed Dec. 20, 2013, both of which are incorporated herein by reference in their entirety.

The present invention relates to the use of diesters of 2,5-dimethyl-2-hexenedioic acid, 2,5-dimethyl-3-hexenedioic acid and 2,5-dimethyladipic acid or a mixture thereof as a fragrance or as flavor, to a method for imparting or modifying a scent or a flavor to a composition by including said compounds into such composition, to a fragrance containing composition and/or a fragrance material containing said compounds and to a process for preparing diesters of 2,5-dimethyladipic acid.

BACKGROUNDOF THE INVENTION

Fragrances are of great interest especially in the field of cosmetics and also laundry and cleaning detergents. Fragrances of natural origin are mostly expensive, often limited in their available amount and, on account of fluctuations in environmental conditions, are also subject to variations in their content, purity etc. It is therefore of great interest to be able to replace, at least partially, fragrances of natural origin with synthetically obtainable substances. Often, in this connection, the natural substance is not replicated chemically, but chemically synthesized compounds are selected as substitutes for natural substances on account of their odor, where substitute and natural substance do not necessarily have to have a chemical- structural similarity.

However, since even small changes in chemical structure may bring about massive changes in the sensory properties such as odor and also taste, the targeted search for substances with certain sensory properties, such as a certain odor, is extremely difficult. The search for new fragrances and flavorings is therefore in most cases difficult and laborious without knowing whether a substance with the desired odor and/or taste will even actually be found.

Diesters of unsaturated and saturated 2,5-dimethyladipic acids and their preparation are generally known in the state of the art.

U.S. Pat. No. 2,244,487 discloses dimethyl (E)-2,5-dimethyl-2-hexenedioate, isolated from high-boiling residues obtained in the manufacturing process of methyl methacrylate using acetone and hydrogen cyanide as raw materials. It is suggested that (E)-2,5-dimethyl-2-hexenedioate can be used for the preparation of resins, plasticizers and as starting material for the preparation of other esters of (E)-2,5-dimethylhex-2-enedioic acid, which in turn are of interest as plasticizers, modifiers or blending agents for synthetic or natural resins.

FR 2 524 341 discloses a palladium catalyst, in form of a allylic cationic complex, for the use in the dimerization or co-dimerization reactions of acrylic acid derivatives with themselves or with mixtures of other di-functional components, such as 1,3-dienes. Besides other dimerization products, the preparation of dimethyl 2-hexendioate from methyl acrylate as well as the preparation of dimethyl 2-methyl-5-methylene-hexanedioate from methyl methacrylate, where dimethyl (E)-2,5-dimethyl-3-hexenedioate was formed as a side product, using the claimed palladium catalyst are exemplified.

DE 3336691 discloses a process for the nickel catalyzed dimerization of acrylic acid derivatives to yield linear unsaturated dicarboxylic acids derivatives and the use of these dicarboxylic acid derivatives as monomers and/or co-monomers in polymer, polycondensation and hydration reactions.

U.S. Pat. No. 4,451,665 discloses a process for dimerizing a lower alkylacrylate or a lower alkyl-methacrylate in the presence of a palladium (II) catalyst to yield mixtures of isomeric linear dimers. In particular, this reaction was used for the preparation of mixtures of linear isomeric dimethyl hexenedioates and dimethyl 2,5-dimethylhexenedioates.

EP 0 632 010 discloses a process for the preparation of dimethyl esters of alpha,omega-dicarboxylic acids from cycloalkanones with dimethylcarbonate in the presence of a nitrogen containing base. Besides the preparation of other dimethyl esters of alpha,omega-dicarboxylic acids, the preparation of the dimethyl ester of 2,5-dimethyladipic acid from 2,5-dimethylcyclopentanone and dimethylcarbonate is exemplified.

Narushi et al., Nippon Kagaku Kaishi 1976, Vol. 11, pp.1794-6, relates to the identification of α-methylene-δ-methyladipic acid (2-methyl-5-methylene-hexanedioic acid) as the main product of a dimerization process comprising the thermal dimerization of calcium methacrylate (monomer salt) followed by treatment of the obtained acidic dimerization products with diazomethane.

Matsuoka et al., Org. Lett. 2011, Vol. 13(14), pp. 3722-5, disclose a process for the selective tail-to-tail dimerization of methyl methacrylate in the presence of an N-heterocyclic carbene catalyst, yielding dimethyl 2,5-dimethyl-2-hexenedioate with an E/Z ratio of 95:5.

Biju et al., Angew. Chem. Int. Ed. Engl. 2011, Vol. 50(36), pp. 8412-5, disclose a process for the coupling of two activated olefins in the presence of an N-heterocyclic carbene catalyst. Their optimized process allows the production of dibutyl 2,5-dimethyl-2-hexenedioate from dibutyl methacrylate with an E/Z ratio of 97:3.

JP 54092636 discloses fragrant compositions containing di-($C_1$-$C_{10}$)-esters of α-methylene-δ-methyladipic acid (2-methyl-5-methylene-hexanedioic acid) as an effective component. Esters of 2,5-dimethylhexenedioic acids or 2,5-dimethyladipic acid are not mentioned.

SUMMARY OF THE INVENTION

It was an object of the present invention to find substances, which can be used as novel fragrances or flavors and which can be synthesized in large-scale from readily obtainable starting materials. In particular, odor-intensive substances having a pleasant odor are sought. In particular substances with fruity and herbal notes are desirable. The novel fragrances or flavors should be free from toxicological concerns.

It was surprisingly found, that the compounds of the general formulae I.a, I.b or II or a mixture thereof

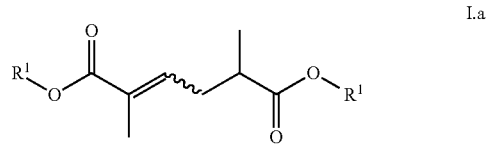

I.a

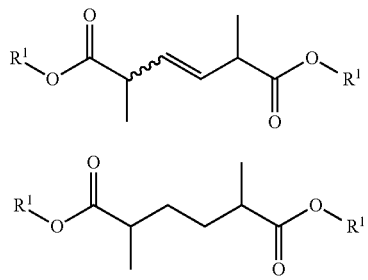

in which
R¹ are identical or different and selected from the group consisting of $C_1$-$C_6$-alkyl and $C_5$-$C_6$-cycloalkyl,
can advantageously be used as a fragrance or as flavor, Therefore, the present invention relates to the use of compounds of formulae I.a, I.b or II, as defined above and hereinafter, or a mixture thereof, as a fragrance or as a flavor.

The invention further relates to the use of compounds I.a, I.b or II or a mixture thereof as a fragrance or as a flavor, where said compounds or mixture are included into compositions, which is selected from laundry detergents, fabric detergents, cosmetic preparations, fragranced hygiene articles, foods, food supplements, fragrance dispensers, perfumes, pharmaceutical preparations and crop protection compositions, and which further comprises a carrier.

The invention further relates to a method of imparting or modifying a scent or a flavor to a composition, which method comprises including a compound of the formulae I.a, I.b or II or a mixture thereof into a composition in such an amount that imparts or modifies the scent or flavor of the composition.

The invention further relates to a fragrance containing composition and/or a fragrance material, which contains at least one compound selected from compounds of the general formulae I.a, I.b and II and mixtures thereof and a carrier material.

The invention further relates to a process for producing compounds of the general formula II and mixtures thereof.

The compounds I.a, I.b and II used according to the present invention exhibit the following advantages:

- The compounds of the general formulae I.a, I.b and II possess advantageous sensory properties, in particular a pleasant odor. Therefore, they can be favorably used as a fragrance or as a flavor or as ingredient of a fragrance containing composition and/or a fragrance material.
- By virtue of their physical properties, the compounds of the general formulae I.a, I.b and II have particularly good, virtually universal solvent properties for other fragrances and other customary ingredients in fragrance-comprising preparations such as, in particular, perfumes.
- The compounds of the general formulae I.a, I.b and II can be synthetically produced by using readily obtainable starting materials, namely $C_1$-$C_6$-alkyl or $C_5$-$C_6$-cycloalkyl esters of methacrylic acid.
- The processes for producing the compounds of the general formulae I.a, I.b and II are simple and efficient. Compounds I.a, I.b and II can therefore be provided without difficulty on a large industrial scale.
- The compounds of the general formulae I.a, I.b and II used according to the present invention are likely to have low toxicity as they represent dimethyl derivatives of virtually non-toxic adipic acid esters and/or 2- or 3-hexenedioic acid esters, respectively.

DETAILED DESCRIPTION

For the purposes of the present invention, the expression "$C_1$-$C_6$-alkyl" comprises straight-chain or branched $C_1$-$C_6$-alkyl groups. Among these are methyl, ethyl, propyl, isopropyl, n-butyl, isobutyl, sec-butyl, tert-butyl, n-pentyl, 2-pentyl, 2-methylbutyl, 3-methylbutyl, 1,2 dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, and the like.

The expression "$C_5$-$C_6$-cycloalkyl" comprises for the purposes of the present invention cyclic hydrocarbons having from 5 to 6, in particular having 6, carbon atoms. Among these are cyclopentyl and cyclohexyl.

Preferred are compounds of the general formulae I.a, I.b or II, in which the moieties R¹ are mutually independently selected from unbranched or branched $C_1$-$C_4$-alkyl.

Further preferred are compounds of the general formulae I.a, I.b or II, in which the moieties R¹ are identical and are selected from unbranched or branched $C_1$-$C_4$-alkyl.

Particularly preferred are compounds of the general formulae I.a, I.b or II, in which the moieties R¹ are identical and are selected from methyl.

Examples of preferred compounds of the general formula I.a are dimethyl 2,5-dimethyl-2-hexenedioate, diethyl 2,5-dimethyl-2-hexenedioate, dibutyl 2,5-dimethyl-2-hexenedioate, in particular dimethyl 2,5-dimethyl-2-hexenedioate.

Examples of preferred compounds of the general formula I.b are dimethyl 2,5-dimethyl-3-hexenedioate, diethyl 2,5-dimethyl-3-hexenedioate, dibutyl 2,5-dimethyl-3-hexenedioate, in particular dimethyl 2,5-dimethyl-3-hexenedioate.

Examples of preferred compounds of the general formula II are dimethyl 2,5-dimethylhexanedioate, diethyl 2,5-dimethylhexanedioate, dibutyl 2,5-dimethylhexanedioate, in particular dimethyl 2,5-dimethylhexanedioate.

The esters of the general formulae I.a and I.b can be present in the form either of pure E-isomers of the formulae I.a-E and I.b-E, respectively, or of pure Z-isomers of the formulae I.a-Z and I.b-Z, respectively, or of E/Z-isomer mixtures.

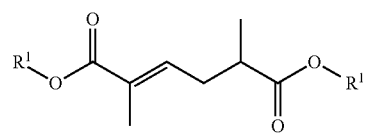

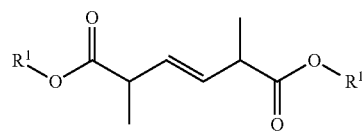

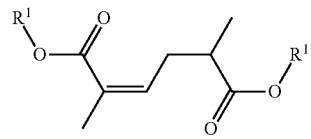

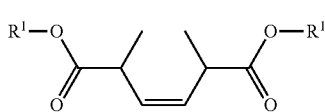
I.b-Z

Often, the esters of the general formulae I.a and I.b are present as E/Z-isomer mixtures. In addition, the E/Z-isomers of compounds I.b (I.b-E and I.b-Z) are typically present as diastereoisomer mixtures of their corresponding D/L- and meso-form. Frequently, the D/L- and meso-form are present in relative amounts ranging from 10:1 to 1:10.

It is preferred that the compounds of the general formulae I.a and/or I.b are predominantly present as their E-isomers of the formulae I.a-E and/or I.b-E. More specifically, the E-isomers of compounds I.a and/or I.b used according to the present invention are present in an amount to at least 60% by weight, in particular to at least 80% by weight, more particularly to at least 90% by weight, based on the total amount of the E- and Z-isomers of I.a and/or I.b.

The esters of the general formulae I.a, I.b and II can be used as a single compound or as a mixture containing two or more of said esters.

In a preferred embodiment, where the compound of formula I.a or a mixture thereof with a compound of formulae I.b and/or II is used, the compound of formula I.a makes up at least 80% by weight, in particular at least 90% by weight, based on the total amount of compounds I.a, I.b and II.

In another preferred embodiment, where the compound of formula II or a mixture thereof with a compound of formulae I.a and/or I.b is used, the compound of formula II makes up at least 80% by weight, in particular at least 90% by weight, based on the total amount of compounds I.a, I.b and II.

In yet a further preferred embodiment, where the compound of formula I.b or a mixture thereof with a compound of formulae I.a and/or II is used, the compound of formula I.b makes up at least 80% by weight, in particular at least 90% by weight, based on the total amount of compounds I.a, I.b and II.

The preferred embodiments mentioned above may be combined arbitrarily with one another.

Accordingly, a particular embodiment of the invention relates to mixtures of compounds of the general formulae I.a, I.b and II, in which the moieties $R^1$ are identical and are selected from unbranched or branched $C_1$-$C_4$-alkyl, where the E-isomers of compounds I.a and/or I.b are present to at least 60% by weight, based on the total amount of the E- and Z-isomers of I.a and/or I.b, and where the compound of formula I.a or a mixture thereof makes up at least 80% by weight, based on the total amount of compounds I.a, I.b and II.

Likewise, a further particular embodiment of the present invention relates to mixtures of compounds of the general formulae I.a, I.b and II, in which the moieties $R^1$ are identical and are selected from unbranched or branched $C_1$-$C_4$-alkyl, where the compound of formula II or a mixture thereof makes up at least 80% by weight, based on the total amount of compounds I.a, I.b and II.

As previously mentioned, it has been found that the compounds of the general formulae I.a, I.b and II possess advantageous sensory properties, in particular a pleasant odor. More specifically, the compounds I.a, I.b and II used according to the present invention generally exhibit intensive odors of largely sweet, fruity, herbal or animal character. This is surprising, since, although these compounds, in particular compounds of the general formula I.a, have long been known in the prior art, their use as a fragrance or flavor has never been reported.

Intensive odor impressions are to be understood as meaning those properties of aroma chemicals which permit a precise perception even in very low gas-space concentrations. The intensity can be ascertained via a threshold-value determination. A threshold value is the concentration of a substance in the relevant gas space at which an odor impression can just still be perceived by a representative test panel, although it no longer has to be defined. The substance class known as probably one of the most odor-intensive, i.e. those with very low threshold values, are thiols, whose threshold value is in the ppb/cbm range. It is the aim of the search for new aroma chemicals to find substances with the lowest possible threshold value in order to permit the lowest possible use concentration. The closer one comes to this target, the more one talks of "intensive" odor substances or aroma chemicals.

"Pleasant odors" or "Advantageous sensory properties" are hedonic expressions which describe the niceness and preciseness of an odor impression conveyed by an aroma chemical.

"Niceness" and "preciseness" are terms which are familiar to the person skilled in the art, a perfumer. Niceness generally refers to a spontaneously brought about, positively perceived, pleasant sensory impression. However, "nice" does not have to be synonymous with "sweet". "Nice" can also describe the odor of musk or sandalwood. "Preciseness" generally refers to a spontaneously brought about sensory impression which—for the same test panel—brings about a reproducibly identical reminder of something specific.

For example, a substance can have an odor which is spontaneously reminiscent of that of an "apple": the odor would then be precisely of "apples". If this apple odor were very pleasant because the odor is reminiscent, for example, of a sweet, fully ripe apple, the odor would be termed "nice". However, the odor of a typically tart apple can also be precise. If both reactions arise upon smelling the substance, in the example thus a nice and precise apple odor, then this substance has particularly advantageous sensory properties.

The invention further relates to the use of the compounds of the general formulae I.a, I.b and II or a mixture thereof, as defined above, in compositions, which typically comprise at least one aroma compound, i.e. at least one fragrance and/or flavoring. Such compositions include, for example, laundry detergents, fabric detergents, cosmetic preparations, other fragranced hygiene articles, such as diapers, sanitary towels, armpit pads, paper towels, wet wipes, toilet paper, pocket tissues, and the like, foods, food supplements, examples being chewing gums or vitamin products, fragrance dispensers, examples being room air fresheners, perfumes, pharmaceutical preparations, and also crop protection products.

Typically, these compositions are formulated by incorporating at least one ester I.a, I.b and II or a mixture thereof, optionally together with one or more other aroma compounds, into an existing preparation, which before comprises no aroma compound or which before comprises one or more other aroma compound different from compounds of the general formulae I.a. I.b and II. Such compositions generally further comprise a carrier, which may be a compound a compound mixture or other additives, which have no or no noticeable sensory properties. The carrier may as well be a compound or an additive having noticeable sensory properties, or a compound mixture comprising one or more other aroma compounds different from compounds I.a, I.b and II and optionally one or more compounds having no or no noticeable sensory properties.

Compounds I.a, I.b and II used in the compositions according to the present invention are usually applied in amounts customary for formulation auxiliaries. More specifically the applied amount of compounds I.a, I.b and II are in the range of 0.001 to 50% by weight, preferably in the range of 0.01 to 20% by weight, more preferably in the range of 0.1 to 10% by weight.

The esters of the general formulae I.a, I.b and II or a mixture thereof preferably find use in laundry detergents and fabric detergents, in cosmetic preparations and in other fragranced hygiene articles. Particular preference is given to the use of esters I.a, I.b and II in cosmetic preparations such as perfumes.

The invention further relates to a method of imparting or modifying a scent or a flavor to a composition, which method comprises including a compound of the formulae I.a, I.b or II or a mixture thereof as defined above into a composition in such an amount that imparts or modifies the scent or flavor of the composition. The total amount of compounds I.a, I.b or II required for modification depends on their respective sensory properties and on the nature of the composition and can therefore vary in a wide range. Typically, the total amount of compounds I.a, I.b and II included into the composition is in the range from 0.001 to 50% by weight, preferably in the range from 0.01 to 20%.

The intensively or precisely smelling substances of the general formulae I.a, I.b and II or a mixture thereof are preferably used as fragrance. Suitable fields of application are all applications in which a certain odor is desired, whether it is to mask more unpleasant odors or to generate a certain odor or certain odor notes in a targeted manner.

Therefore, the invention further relates to a fragrance containing composition and/or a fragrance material, which contains at least one compound selected from compounds of the general formulae I.a, I.b and II and mixtures thereof and a carrier material.

The total concentration of the at least one ester I.a, I.b and II in the fragrance containing composition and/or the fragrance material according to the present invention is not particularly limited. It can be changed in a wide range, depending on the purpose of their use. Generally, amounts that are customary for fragrances are used. The total amount of esters I.a, I.b and II in the fragrance containing composition and/or the fragrance material is typically in the range from 0.001 to 20% by weight, preferably in the range from 0.01 to 10% by weight.

The carrier material may be a compound, a compound mixture or other additives having the properties as defined above. Suitable carrier materials generally comprise liquid or oil-based carrier materials as well as wax-like or solid carrier materials.

Suitable liquid or oil-based carrier materials are for example selected from water, alcohols, such as ethanol, dials and polyols having melting temperatures below 20° C., such as ethylene glycol, diglycerol, propylene glycol, dipropylen glycol, cyclic siloxanes (silicon fluids), such as hexamethylcyclotrisiloxane or decamethylcyclopentasiloxane, plant-oils, such as fractionated coconut-oil, or esters of fatty alcohol having melting temperatures below 20° C., such as isopropyl-myristate.

Suitable wax-like or solid carrier materials are for example selected from fatty alcohols having melting temperatures above 20° C., such as myristyl alcohol, stearyl alcohol or cetyl alcohol, polyols and esters of fatty alcohol having melting temperatures above 20° C., synthetic petroleum derived waxes, such as paraffin waxes, water insoluble porous minerals, such as silica, silicates, for example talc, microporous aluminasilicate minerals (zeolites), clay minerals, for example bentonite, or phosphates for example sodium tripolyphosphate, paper, cardboard, wood, nonwoven of rayon staple fibers or fiber-fleeces.

Suitable carrier materials are for example also selected from water-soluble polymers, such as polyacrylic acid esters or quaternized polyvinyl pyrrolidone or water-alcohol-soluble polymers, such as specific thermoplastic polyesters and polyamides. The polymeric carrier material can be present in different forms, for example in form of a gel, a paste, or water insoluble solid particles, such as microcapsules or friable coatings.

Depending on the purpose of use, the carrier materials may further comprise other additives or auxiliaries, for example surfactants or mixtures of surfactants, viscosifiers, such as polyethylene glycols with a molecular weight of 400 to 20'000 Da, lubricates, binding or agglomerating agents, such as sodium silicate, dispersing agents, detergent builder salts, filler salts, pigments, dyes, optical brighteners, anti-redeposition agents and the like.

Typical applications of the composition and/or the fragrance material according to the present invention are in the field of laundry and cleaning detergents, preparations of fragrances for the human or animal body, for rooms such as kitchens, wet rooms, automobiles or heavy goods vehicles, for real or artificial plants, for clothing, for shoes and shoe insoles, for items of furniture, for carpets, for air humidifiers and air fresheners, for cosmetics, such as perfumes.

The invention also includes odorant combinations, which comprise at least one ester of the formulae I.a, I.b and II for use in accordance with the invention, more particularly at least one of the esters of the formulae I.a, I.b and II said to be preferred, as component A and at least one further compound known as an odorant or aroma substance, as component B, such as, for example, one or more of the following compounds B1 to B11:

B1: methyl dihydrojasmonate (e.g. hedione),
B2: 4,6,6,7,8,8-hexamethyl-1,3,4,6,7,8-hexahydrocyclopenta[g]benzopyran (e.g. Galaxolide™),
B3: 2-methyl-3-(4-tert-butylphenyl)propanal (Lysmeral™),
B4: 2-methyl-3-(4-isopropylphenyl)propanal (cyclamenaldehyde),
B5: 2,6-dimethyl-7-octen-2-ol (dihydromyrcenol),
B6: 3,7-dimethyl-1,6-octadien-3-ol (linalool),
B7: 3,7-dimethyl-trans-2,6-octadien-1-ol (geraniol),
B8: 2,3,8,8-tetramethyl-1,2,3,4,5,6,7,8-octahydro-2-naphthalenyl methyl ketone (Iso E Super™),
B9: alpha-hexylcinnamaldehyde,
B10: 3,7-dimethyl-6-octen-1-ol (citronellol),
B11: alpha- or beta- or delta-damascone.

Suitable formulations of odor substances are, for example, the formulations disclosed in JP 11-071312 A, paragraphs [0090] to [0092]. The formulations from JP 11-035969 A, paragraphs [0039] to [0043] are also likewise suitable.

The invention further provides a process for preparing a compound of the formula II or a mixture thereof as defined above, which comprises i. dimerizing a methacrylate ester of the general formula III

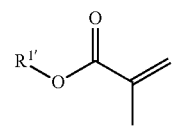

wherein R[1'] has one of the meanings given for R[1] in the presence of at least one N-heterocyclic carbene catalyst to yield a compound of the general formulae I.a or I.b or a mixture thereof, where R[1] has the meaning of R[1'];

ii. catalytic hydrogenation to yield the compound of the general formula (II), where R[1] has the meaning of R[1'].

In respect of suitable and preferred embodiments of the moieties R[1] and R[1'], reference is made to the disclosure provided above.

The dimerization reaction (step i.) is principally known in the art. Suitable reaction conditions have been described, e.g. by Matsuoka et al., Org. Lett. 2011, Vol. 13(14), pp. 3722-5 and Biju et al., Angew. Chem. Int. Ed. Engl. 2011, Vol. 50(36), pp. 8412-5.

Suitable N-heterocyclic carbene catalyst, which can be used to catalyze the dimerization of monomer compounds III, and methods for their generation are for example described in EP 0587044 A2 and by Enders et al., Angew. Chem. Int. Ed. 1995, Vol. 34(9), pp. 1021-1023.

Preferably, the N-heterocyclic carbene catalyst is selected from compounds of the general formula V

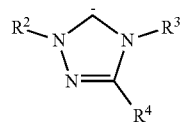

V in which

R[2] and R[3] are independently selected from the group consisting of $C_1$-$C_6$-alkyl, aryl and heteroaryl, where aryl and heteroaryl are unsubstituted or substituted by 1, 2, 3 or 4 radicals selected from the group consisting of $C_1$-$C_4$-alkyl, $C_1$-$C_4$-haloalkyl, $C_1$-$C_4$-alkoxy and halogen;

R[4] is selected from the group consisting of $C_1$-$C_{12}$-alkyl, $C_1$-$C_{12}$-alkoxy, $C_1$-$C_6$-haloalkyl, —NR[5]R[6], halogen, aryloxy, aryl and heteroaryl, where aryloxy, aryl and heteroaryl are unsubstituted or substituted by 1, 2, 3 or 4 radicals selected from the group consisting of $C_1$-$C_4$-alkyl, $C_1$-$C_4$-alkoxy and halogen;

R[5] is selected from the group consisting of hydrogen, $C_1$-$C_{12}$-alkyl and aryl;

R[6] is selected from the group consisting of $C_1$-$C_{12}$-alkyl and aryl.

More preferred, the N-heterocyclic carbene catalyst used in the dimerization step of the process according to the present invention is selected from compounds of the general formula V, where R[2], R[3] and R[4] are independently selected from phenyl, which can be optionally substituted by 1, 2, or 3 radicals selected from the group consisting of $C_1$-$C_4$-alkyl, $C_1$-$C_4$-alkoxy and halogen.

Particularly preferred is a N-heterocyclic carbene catalyst of the general formula V, where the substituents R[2], R[3] and R[4] are phenyl.

Typically, the N-heterocyclic carbene catalyst is generated in-situ from a methoxytriazolin precursor of the general formula (IV)

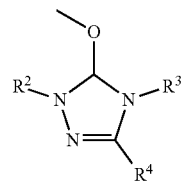

IV in which R[2], R[3] and R[4] are as defined above, by heating the precursor (IV) in the absence of any diluent under reduced pressure.

The pressure applied for the in-situ generation of the carbene catalyst V from precursor IV is preferably in the range from 0.01 to 10 mbar, in particular in the range from 0.1 to 5 mbar.

The temperature used for the in-situ generation of the carbene catalyst V from precursor IV is in the range from 20 to 200° C., preferably from 40 to 160° C., in particular in the range from 50 to 110° C.

Generally, the N-heterocyclic carbene catalyst (V) is used in an amount from 0.1 to 10 mol-%, preferably 0.5 to 5 mol-%, based on the methacrylate ester of formula III.

The dimerization reaction is usually carried out in the temperature range from 20 to 200° C., preferably from 40 to 160° C., in particular in the range from 50 to 110° C.

The dimerization reaction can generally take place at ambient pressure or at reduced or elevated pressure. It is preferable that the dimerization reaction is carried out at ambient pressure or reduced pressure.

The dimerization reaction can be carried out in the absence of any added solvent or in the presence of an organic solvent.

If the dimerization reaction is carried out in the presence of a solvent, it is preferable that the organic solvent used is inert under the reaction conditions. Among these are by way of example aliphatic hydrocarbons, halogenated aliphatic hydrocarbons, and aromatic and substituted aromatic hydrocarbons and ethers. It is preferable that the solvent is one selected from pentane, hexane, heptane, ligroin, petrol ether, cyclohexane, dichloromethane, trichloromethane, tetrachloromethane, benzene, toluene, xylene, chlorobenzene, dichlorobenzenes, dibutyl ether, THF, 1,4-dioxane, 1,2-dimethoxyethane and mixtures thereof.

If the dimerization reaction is carried out in the presence of an inert organic solvent, the amount of the solvent in the reaction mixture is preferably less than 10% by weight, based on the amount of compound III.

The dimerization reaction can take place in the absence of or in the presence of an inert gas. The expression inert gas generally means a gas, which under the prevailing reaction conditions does not enter into any reactions with the starting materials, reagents, or solvents participating in the reaction, or with the resultant products. It is preferable that the dimerization reaction takes place without addition of any inert gas.

After completion of the dimerization reaction, any unconverted starting material (compound III) is preferably removed from the reaction mixture, e.g. by distillation. The distillation column necessary for this purpose generally has direct connection to the dimerization reactor, and it is preferable that said column is a direct attachment thereto. If desired, the recovered starting material (compound III) can be used for the next reaction.

Typically, the dimerization products are further purified by distillation or by using chromatographic methods. Preferably, the products I.a and I.b are purified by distillation.

The dimerization reaction of the present process (step i.) provides the ester compounds I.a and I.b in high yields and selectivity. In particular, no esters of 2-methyl-5-methylene-hexanedioic acid are detectable within the detection limits of the gas-chromatographic method used for analyzing the purity and composition of the dimerization products. The detection limit of the used gas-chromatographic analysis system is estimated to be about 10 wt.-ppm.

The catalytic hydrogenation of the unsaturated dimerization products I.a and I.b, corresponding to step ii. of the present process, is carried out using processes and catalysts for the hydrogenation of double bonds that are well known to the person skilled in the art.

Suitable catalysts for the hydrogenation of double bonds are for example catalysts, which comprise at least one metal of transition group VIII of the Periodic Table of the Elements, for example platinum, rhodium, palladium, cobalt, nickel, or ruthenium, preferably ruthenium, either alone or together with at least one metal from transition group I or VII of the Periodic Table of the Elements, for example copper or ruthenium, typically deposited on a support material. Suitable support materials are by way of example zirconium dioxide ($ZrO_2$), zinc oxide (ZnO), magnesium oxide (MgO), sulfated zirconium dioxide, tungsten carbide (WC), titanium dioxide ($TiO_2$), sulfated carbon, activated charcoal, diatomite, clay, aluminium oxide, aluminium phosphate, aluminosilicates, such as zeolites, or phosphated aluminium oxide, silicium dioxide or else a combination thereof. Other suitable catalysts are likewise Raney catalysts, preferably Raney nickel.

The hydrogenation can take place by analogy with known hydrogenation processes for hydrogenating organic compounds which have hydrogenatable groups. To this end, the organic compound in the form of liquid phase or gas phase, preferably in the form of liquid phase, is brought into contact with the catalyst in the presence of hydrogen. The liquid phase can by way of example be passed over a fluidized bed of catalyst (fluidized bed method) or can be passed over a fixed bed of catalyst (fixed bed method).

In the process of the invention, it is preferable that the hydrogenation takes place in a fixed-bed reactor.

The hydrogenation can be designed to take place either continuously or else batchwise, preference being given here to the continuous design of the process. The batchwise hydrogenation can use a reaction apparatus conventionally used for this purpose, e.g. a stirred reactor. It is preferable that the hydrogenation of the invention is carried out continuously in fixed-bed reactors in upflow mode or downflow mode. The hydrogen here can be passed over the catalyst co-currently with the solution of the starting material to be hydrogenated, or else in countercurrent.

Suitable apparatuses for conducting fluidized-bed-catalyst hydrogenation and fixed-bed-catalyst hydrogenation are known in the prior art, e.g. from Ullmanns Enzyklopadie der Technischen Chemie [Ullmann's Encyclopedia of Industrial Chemistry], $4^{th}$ edition, volume 13, pp. 135 ff., and also from P. N. Rylander, "Hydrogenation and Dehydrogenation" in Ullmann's Encyclopedia of Industrial Chemistry, 5th edn. on CD-ROM.

The hydrogenation generally takes place under elevated hydrogen pressure. Preference is given to hydrogen pressure in the range from 2 to 400 bar, particularly from 5 to 300 bar.

It is preferable that the hydrogenation takes place in the presence of an organic solvent that is inert under the hydrogenation conditions. Suitable solvents are those previously defined for the dimerization reaction. Specifically, an ether is used, for example THF, or a dialkylene glycol, or a mono- or diether thereof, for example glyme.

The hydrogenation is carried out at a temperature in the range from 20 to 300° C., particularly preferably from 40 to 200° C.

The amount of hydrogen used for the hydrogenation is generally from 1 to 15 times the stoichiometric amount of hydrogen theoretically needed for the complete hydrogenation of the double bond of the saturated esters I.a and I.b.

In one preferred embodiment of step ii. of the present process, the hydrogenation is carried out with a Raney catalyst, in particular Raney nickel, applied in an amount of from 0.1 to 10% by weight, in the presence of an inert solvent, under hydrogen pressure of from 10 to 150 bar, at a temperature of from 50 to 150° C.

The processes according to the present invention further comprises subjecting a compound of the formulae I.a, I.b and II and mixtures thereof to a transesterification with an alcohol of formula $R^1$—OH, where $R^1$ is as defined above but is different from the radical $R^{1'}$ in the methacrylate ester of formula III used in the dimerization.

Conventional processes known to the person skilled in the art can be used for the transesterification reactions.

The transesterification used in the process according to the present invention is typically carried out in the presence of a suitable transesterification catalyst. Suitable transesterification catalysts are the conventional catalysts usually used for transesterification reactions, where these are mostly also used in esterification reactions. Among these are by way of example mineral acids, such as sulfuric acid and phosphoric acid; organic sulfonic acids, such as methanesulfonic acid and p-toluenesulfonic acid; and specific metal catalysts from the group of the tin(IV) catalysts, for example dialkyltin dicarboxylates, such as dibutyltin diacetate, trialkyltin alkoxides, monoalkyltin compounds, such as monobutyltin dioxide, tin salts, such as tin acetate, or tin oxides; from the group of the titanium catalysts: monomeric and polymeric titanates and titanium chelates, for example tetraethyl orthotitanate, tetrapropyl orthotitanate, tetrabutyl orthotitanate, triethanolamine titanate; from the group of the zirconium catalysts: zirconates and zirconium chelates, for example tetrapropyl zirconate, tetrabutyl zirconate, triethanolamine zirconate; and also lithium catalysts, such as lithium salts, lithium alkoxides; and aluminum(III) acetylacetonate, chromium(III) acetylacetonate, iron(III) acetylacetonate, cobalt (II) acetylacetonate, nickel(II) acetylacetonate, and zinc(II) acetylacetonate.

The amount of transesterification catalyst used is from 0.001 to 10% by weight, preferably from 0.05 to 5% by weight, The reaction mixture is preferably heated to the boiling point of the reaction mixture, the reaction temperature therefore being from 20° C. to 200° C., depending on the reactants.

The transesterification can take place at ambient pressure or at reduced or elevated pressure. It is preferable that the transesterification is carried out at a pressure from 0.001 to 200 bar, particularly from 0.01 to 5 bar. The relatively low-boiling-point alcohol eliminated during the transesterification is preferably continuously removed by distillation in order to shift the equilibrium of the transesterification reaction. The distillation column necessary for this purpose generally has direct connection to the transesterification reactor, and it is preferable that said column is a direct attachment thereto. If a plurality of transesterification reactors are used in series, each of said reactors can have a distillation column, or the vaporized alcohol mixture can preferably be introduced into a distillation column from the final tanks of the transesterification reactor cascade by way of one or more collection lines. The relatively high-boiling-point alcohol reclaimed in said distillation is preferably returned to the transesterification.

If an amphoteric catalyst is used, this is generally successfully removed via hydrolysis and subsequent removal of the metal oxide formed, for example by filtration. It is preferable that, once the reaction has taken place, the catalyst is hydrolyzed by washing with water, and that the precipitated metal oxide is removed by filtration. If desired, the filtrate may be subjected to further workup for isolation and/or purification of the product. The product is preferably isolated by distillation.

The transesterification can be carried out in the absence of, or in the presence of, an added organic solvent. It is preferable that the transesterification is carried out in the presence of an inert organic solvent. Suitable organic solvents are those mentioned above for the dimerization reaction. Among these are specifically toluene and THF.

The transesterification is preferably carried out in the temperature range from 50 to 200° C.

The transesterification can take place in the absence of or in the presence of an inert gas. It is preferable that the transesterification takes place without addition of any inert gas.

The examples below provide further explanation of the invention. These figures and examples are not to be understood as restricting the invention.

EXAMPLES

I) Gas Chromatographic Analysis
GC-System and Separation Method:
GC-system: Agilent 7890A
GC-Column: HP-5 (60 m (Length), 0.32 mm (ID), 1.0 µm (Film))
Temperature program: 100° C. to 225° C. in 5° C./min, 10 minutes at 225° C., 225° C. to until 280° C. in 5° C./min.
II) Production Examples Example II.1

Synthesis of dimethylesters of
2,5-dimethyl-2-hexenedioic acid and
2,5-dimethyl-3-hexenedioic Acid via Dimerization
of methylmethacrylate.

II.1.1 Generation of the N-Heterocyclic Carbene Catalyst:
6.53 g 3-methoxy-2,4,5-triphenyl-3H-1,2,4-triazole (0.02 mol) was placed into a glass reactor equipped with heating jacket, mechanical stirrer and a vacuum line with implemented cold trap. The solid was heated at 80° C. for 20 hours under vacuum (ca. 1 mbar). The resulting carbene catalyst was directly used for the dimerization reaction, without work-up or purification.
II.1.2 Dimerization Reaction:
To 0.02 mol of the carbene catalyst, prepared according to example II.1.1, 100 g methylmethacrylate (1.0 mol obtained from Aldrich Chemicals) was added. The resulting solution was then heated at 80° C. for 4 hours. Unconverted methylmethacrylate was distilled off under reduced pressure and the remaining product was rectified (boiling point: 85° C. at <1 mbar) to obtain 48 g (48% yield) methylesters of 2,5-dimethyl-2-hexenedioic acid and 2,5-dimethyl-2-hexenedioic acid of the following composition (=Product I):

| | |
|---|---|
| dimethyl (E)-2,5-dimethyl-2-hexenedioate | 92.0% |
| dimethyl (Z)-2,5-dimethyl-2-hexenedioate | 6.0% |
| dimethyl (E)-2,5-dimethyl-3-hexenedioate (1:1 mixture of DL- and meso-diastereoisomers) | 1.9% |
| dimethyl (Z)-2,5-dimethyl-3-hexenedioate (1:1 mixture of DL- and meso-diastereoisomers) | 0.1% |

The purity of the methylester composition (Product I) was 99.7%.

The purity and composition of the dimerization product was determined using gas chromatography and $^1$H- and $^{13}$C-NMR.

Example II.2

Synthesis of dimethyl 2,5-dimethyladipate.

100 g (0.5 mol) of the methylester composition of example II.1 (Product I) was placed into a hydrogenation reactor and 5 wt. % Raney nickel was added. The mixture was heated at 100° C. under a hydrogen pressure of 30 bar for 2 hours. Following this, the reaction mixture was filtered, yielding 100 g of dimethyl 2,5-dimethyladipate (99% yield) of 99.7% purity. The purity of the product (=Product 2) was determined using gas chromatography and $^1$H- and $^{13}$C-NMR.

Example II.3

Synthesis of diethylesters of
2,5-dimethyl-2-hexenedioic acid and
2,5-dimethyl-3-hexenedioic Acid via
Transesterification of the Dimerization Product of
Example II.1 (Product I).

The diethylesters of 2,5-dimethyl-2-hexenedioic acid and 2,5-dimethyl-3-hexenedioic acid were prepared from the dimerization product of example II.1 (Product I) and ethanol by a standard transesterification procedure well known to the skilled person. After completion of the transesterification reaction, the crude transesterification product was purified by means of fractional distillation (boiling point: 93° C. at <1 mbar), whereupon the diethylester of Product I was obtained in the form of clear colorless liquid in a purity of 97.1%. The identity and purity of the final product was determined by means of GC-MS.

Example II.4

Synthesis of dibutylesters of
2,5-dimethyl-2-hexenedioic acid and
2,5-dimethyl-3-hexenedioic Acid via
Transesterification of the Dimerization Product of
Example II.1 (Product I).

The dibutylesters of 2,5-dimethyl-2-hexenedioic acid and 2,5-dimethyl-3-hexenedioic acid were prepared from the dimerization product of example II.1 (Product I) and n-butanol by a standard transesterification procedure well known to the skilled person. After completion of the transesterification reaction, the crude transesterification product was purified by means of fractional distillation (boiling point: 136° C. at <1 mbar), whereupon the dibutylester of Product I was obtained in the form of clear colorless liquid in a purity of 99.8%. The identity and purity of the final product was determined by means of GC-MS.

Example II.5

Synthesis of the diethylester of 2,5-dimethyladipic Acid via Transesterification of the Product of Example II.2 (Product II).

The diethylester of 2,5-dimethyladipic acid was prepared from the dimerization product of example II.2 (Product II) and ethanol by standard transesterification procedure well known to the skilled person. After completion of the transesterification reaction, the crude transesterification product was purified by means of fractional distillation (boiling point: 71° C. at <1 mbar), whereupon the diethylester of Product II was obtained in the form of clear colorless liquid in a purity of 98.1%. The identity and purity of the final product was determined by means of GC-MS.

Example II.6

Synthesis of the dibutylester of 2,5-dimethyladipic Acid via Transesterification of the Product of Example II.2 (Product II).

The dibutylester of 2,5-dimethyladipic acid was prepared from the dimerization product of example II.2 (Product II) and n-butanol by standard transesterification procedure well known to the skilled person. After completion of the transesterification reaction, the crude transesterification product was purified by means of fractional distillation (boiling point: 123° C. at <1 mbar), whereupon the dibutylester of Product II was obtained in the form of clear colorless liquid in a purity of 99.8%. The identity and purity of the final product was determined by means of GC-MS.

III) Scent Strip Tests

To evaluate the quality and intensity of the odor of compounds I.a, I.b and II used according to the present invention, scent strip tests were performed.

For this purpose, strips of absorbent paper were dipped into solution containing 0.01 to 10 wt.-% of esters I.a, I.b and II prepared according to examples II.1 to II.6. After evaporation of the solvent (about 5 to 10 sec.) the scent impression was olfactorically evaluated by a trained perfumer.

III.1: Results of Scent Strip Test of Unsaturated Esters Used According to the Present Invention (Esters of Product I).

Dimethylester (Product of Example II.1):

| Time elapsed | Odor impression |
| --- | --- |
| <1 min. | gob odor, fruity (banana) |
| 10 min. | gob-sulfurous odor, fruity (banana) |
| 1 h | gob odor, fruity (banana) |
| 24 h | fruity (banana) |

Diethylester (Product of Example II.2):

| Time elapsed | Odor impression |
| --- | --- |
| <1 min. | weakly fermenting smell |
| 10 min. | sweet, fruity (banana) |
| 1 h | sweet, fruity (banana) |
| 24 h | sweet, fruity (banana) |

Dibutylester (Product of Example II.3):

| Time elapsed | Odor impression |
| --- | --- |
| <1 min. | moldy, week |
| 10 min. | moldy, week |
| 1 h | very slightly moldy |
| 24 h | almost odorless |

III.2: Results of Scent Strip Test of Saturated Esters Used According to the Present Invention (Esters of Product II).

Dimethylester (Product of Example II.4):

| Time elapsed | Odor impression |
| --- | --- |
| <1 min. | fresh, fruity, green, herbal |
| 10 min. | fresh, fruity, green, herbal |
| 1 h | fresh, fruity, green, herbal |
| 24 h | almost odorless |

Diesthylester (Product of Example II.5):

| Time elapsed | Odor impression |
| --- | --- |
| <1 min. | fruity (banana) |
| 10 min. | fruity (banana) |
| 1 h | fruity (banana), moldy (stone fruit schnapps) |
| 24 h | almost odorless |

Dibutylester (Product of Example II.6):

| Time elapsed | Odor impression |
| --- | --- |
| <1 min. | animal (phenylacetic acid) |
| 10 min. | animal (phenylacetic acid) |
| 1 h | animal (phenylacetic acid) |
| 24 h | almost odorless |

The invention claimed is:

1. A fragrance or a flavor which comprises a compound of the general formulae I.b or II or a mixture thereof

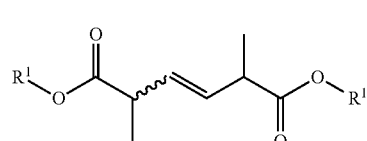

I.b

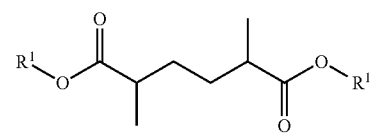

II wherein
R$^1$ are identical or different and selected from the group consisting of $C_1$-$C_6$-alkyl and $C_5$-$C_6$-cycloalkyl.

2. The fragrance or a flavor of claim 1, where both R$^1$ are selected from $C_1$-$C_4$-alkyl.

3. The fragrance or a flavor of claim 1, where both R$^1$ are identical.

4. The fragrance or a flavor of claim 1, where both R$^1$ are methyl.

5. The fragrance or a flavor of claim 1, wherein the fragrance optionally contains a compound of the general formula I.a,

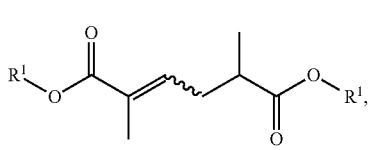
(I.a)

wherein the compounds of formula I.a and/or I.b are predominately present as their E-isomers of the formula I.a-E and/or I.b-E,

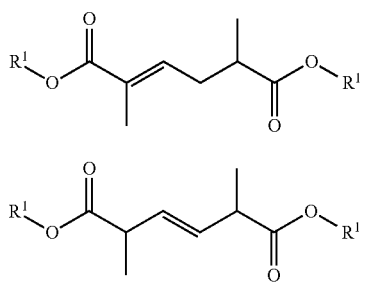

I.a-E

I.b-E wherein $R^1$ are identical or different and selected from the group consisting of $C_1$-$C_6$-alkyl and $C_5$-$C_6$-cycloalkyl.

6. The fragrance or a flavor of claim 1, where the fragrance optionally contains a compound of the general formula I.a,

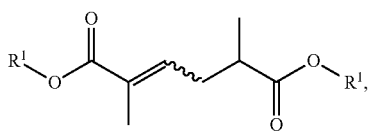
(I.a)

where the compound of formula II or a mixture thereof with a compound of formulae I.a and/or I.b is used, where the compound of formula II makes up at least 80%, based on the total amount of compounds I.a, I.b and II.

7. The fragrance or a flavor of claim 1, where the fragrance optionally contains a compound of the general formula I.a,

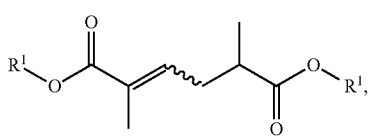
(I.a)

where the compound of formula I.b or a mixture thereof with a compound of formulae I.a and/or II is used, where the compound of formula I.b makes up at least 80%, based on the total amount of compounds I.a, I.b and II.

8. The fragrance or a flavor of claim 1, wherein the fragrance optionally contains a compound of the general formula I.a,

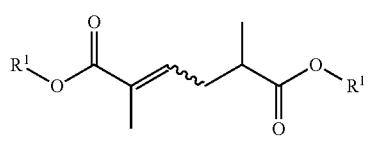
(I.a)

where the compounds of formulae I.a, I.b or II or a mixture thereof is incorporated into a composition, further comprising a carrier.

9. The fragrance or a flavor of claim 8, where the composition is selected from laundry detergents, fabric detergents, cosmetic preparations, fragranced hygiene articles, foods, food supplements, fragrance dispensers, perfumes, pharmaceutical preparations and crop protection compositions.

10. A fragrance composition as claimed in claim 1 which further comprises a carrier material.

11. The fragrance or a flavor of claim 1 further comprises a compound of formula I.a

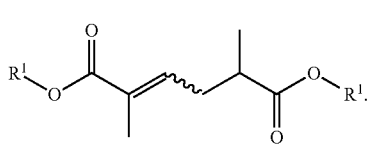
(I.a)

12. The fragrance or a flavor of claim 11, wherein a mixture of compound I.a with a compound of formulae I.b and/or II is used, where the compound of formula I.a makes up at least 80%, based on the total amount of compounds I.a, I.b and II.

13. The fragrance or a flavor of claim 11, where both $R^1$ are selected from $C_1$-$C_4$-alkyl.

14. The fragrance or a flavor of claim 11, where both $R^1$ are identical.

15. The fragrance or a flavor of claim 11, where both $R^1$ are methyl.

16. The fragrance or a flavor of claim 11, where the compounds of formula I.a and/or I.b are predominately present as their E-isomers of the formula I.a-E and/or I.b-E,

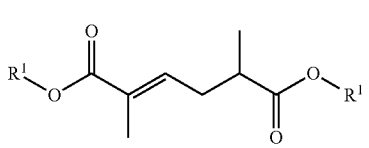
I.a-E

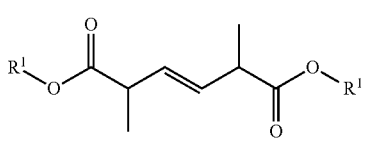
I.b-E wherein $R^1$ are identical or different and selected from the group consisting of $C_1$-$C_6$-alkyl and $C_5$-$C_6$-cycloalkyl.

17. The fragrance or a flavor of claim 11, where the composition is selected from laundry detergents, fabric detergents, cosmetic preparations, fragranced hygiene articles, foods, food supplements, fragrance dispensers, perfumes, pharmaceutical preparations and crop protection compositions.

18. A method of imparting or modifying a scent or a flavor to a composition, which method comprises incorporating a compound of the formulae I.a, I.b or II or a mixture thereof

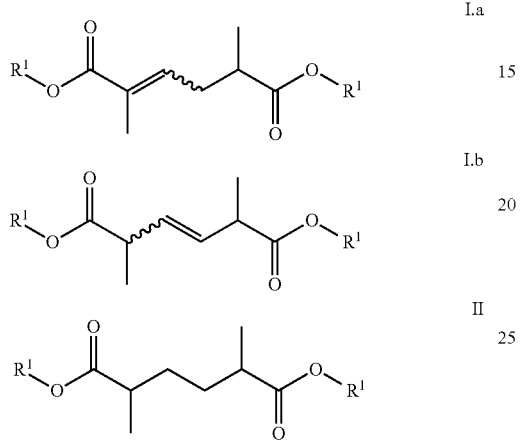

wherein $R^1$ are identical or different and selected from the group consisting of $C_1$-$C_6$-alkyl and $C_5$-$C_6$-cycloalkyl, into a composition in such an amount that imparts or modifies the scent or flavor of the composition.

19. A process for preparing a compound of the formula II

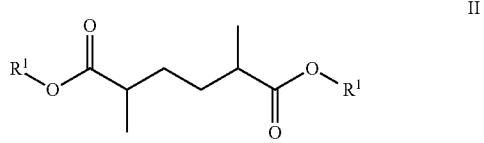

wherein $R^1$ are identical or different and selected from the group consisting of $C_1$-$C_6$-alkyl and $C_5$-$C_6$-cycloalkyl, which comprises i. dimerizing a methacrylate ester of the general formula III

wherein $R^{1\prime}$ has one of the meanings given for $R^1$ in the presence of at least one N-heterocyclic carbene catalyst to yield a compound of the general formulae I.a or I.b or a mixture thereof, where $R^1$ has the meaning of $R^{1\prime}$;

ii. catalytic hydrogenation to yield the compound of the general formula (II), where $R^1$ has the meaning of $R^{1\prime}$.

20. The process of claim 19, which further comprises subjecting the compound of the formulae I.a, I.b and II and mixtures thereof to a transesterification with an alcohol of formula $R^1$—OH, where $R^1$ is as defined above but is different from the radical $R^{1\prime}$ in the methacrylate ester of formula III used in the dimerization.

* * * * *